US012402891B2

(12) United States Patent
Firmbach et al.

(10) Patent No.: US 12,402,891 B2
(45) Date of Patent: Sep. 2, 2025

(54) SURGICAL INSTRUMENT

(71) Applicant: Aesculap AG, Tuttlingen (DE)

(72) Inventors: Franz-Peter Firmbach, Emmingen-Liptingen (DE); Svenja Anhorn, Heroldstatt (DE)

(73) Assignee: Aesculap AG, Tuttlingen (DE)

( * ) Notice: Subject to any disclaimer, the term of this patent is extended or adjusted under 35 U.S.C. 154(b) by 332 days.

(21) Appl. No.: 18/112,569

(22) Filed: Feb. 22, 2023

(65) Prior Publication Data

US 2023/0285032 A1 Sep. 14, 2023

(30) Foreign Application Priority Data

Mar. 8, 2022 (DE) ...................... 10 2022 2023 14.5

(51) Int. Cl.
*A61B 17/15* (2006.01)
*A61B 17/17* (2006.01)
*A61F 2/38* (2006.01)

(52) U.S. Cl.
CPC ........ *A61B 17/155* (2013.01); *A61B 17/1764* (2013.01); *A61F 2/3859* (2013.01)

(58) Field of Classification Search
CPC .. A61B 17/155; A61B 17/1764; A61F 2/3859
See application file for complete search history.

(56) References Cited

U.S. PATENT DOCUMENTS

| 5,925,049 | A | 7/1999 | Gustilo et al. |
| 9,693,788 | B2 | 7/2017 | Metzger et al. |
| 2014/0364857 | A1 | 12/2014 | Bojarski et al. |
| 2016/0199134 | A1* | 7/2016 | Brown .................. A61F 2/4607 606/89 |

FOREIGN PATENT DOCUMENTS

WO 9400056 A1 1/1994

* cited by examiner

*Primary Examiner* — Sameh R Boles
(74) *Attorney, Agent, or Firm* — Christopher A. Rothe; CM Law (57) ABSTRACT

A surgical instrument includes a cutting block with a rear face configured to bear on a distal end face of a resected femur. The cutting block has a guide slot extending from the rear face to a front face. The guide slot is configured to receive and guide a saw blade. A reference foot is mountable on a lower face of the cutting block, and has an anteriorly oriented foot upper face that, in a mounted state of the reference foot, protrudes beyond the rear face and is configured to bear on posterior condyles of the femur. A probe is mountable on the cutting block, in a region of a block upper face lying opposite the block lower face, and has a probe tip which, in a mounted state of the probe, protrudes beyond the rear face and is configured to bear on an anterior face of the femur.

16 Claims, 11 Drawing Sheets

SURGICAL INSTRUMENT

CROSS-REFERENCE TO RELATED APPLICATION

This application claims priority under 35 U.S.C. § 119 to German Application No. 102022202314.5, filed Mar. 8, 2022, the content of which is incorporated by reference herein in its entirety.

FIELD

The present disclosure relates to a surgical instrument for use in a knee joint replacement operation.

BACKGROUND

The use of orthopaedic prostheses as artificial replacements for damaged or worn natural bone structures is common medical practice. In particular, hip joint and knee joint replacement operations are nowadays routine in surgical orthopaedics.

In a knee joint replacement operation, or total knee arthroplasty, joint surfaces of the femur and/or tibia that have become worn or have been otherwise affected by disease or by injury are replaced by a knee joint prosthesis. Such knee joint prostheses usually comprise a femoral component, which is implanted at the distal end of the femur, and a tibial component, which is implanted at the proximal end of the tibia. In order to ensure proper functioning of the artificial replacement joint, the aforementioned components have to be placed as precisely as possible in a defined position and orientation with respect to the anatomy of the patient and to the axes of the body. Otherwise, a result must be expected that is unsatisfactory for the patient. There are different surgical approaches as regards the positioning of the components.

In an approach known as mechanical alignment, which has been the approach mainly used hitherto, the position and orientation of the artificial joint axes of the knee joint prosthesis have been provided so as to be mechanically ideal, without consideration being given to any orthopaedic deformities of the patient. The longitudinal axis of the tibia has often been used here as a reference axis for the orientation and positioning. Clinical studies have shown that the mechanical alignment approach can lead to the function of the artificial knee joint being felt unnatural.

A further approach is what is known as kinematic alignment. In this technique, the femoral component and the tibial component are positioned taking into consideration any orthopaedic deformities of the patient. The aim is to restore the patient's natural joint orientation, which in some cases is affected by deformity. Clinical studies have shown that the kinematic alignment approach is often associated with improved patient satisfaction. In particular, the function of the artificial knee joint is felt by the patient to be more natural.

In addition to the precise positioning, it is important that the femoral component and the tibial component are each selected and implanted in a size that is appropriate to the anatomy of the patient. The size of the femoral component depends broadly on the size of the femur, the size being determined intraoperatively using a measurement instrument provided for this purpose. Such measurement instruments are also referred to as femoral sizers or femoral sizing systems.

It is customary to determine the size after the resection of the distal femur. The known measurement instrument is placed onto the resected end face of the distal femur and oriented with respect to anatomical reference surfaces or anatomical landmarks. After the size has been determined, the distal femur is prepared further for the application of the femoral component. This requires further resection, which usually comprises an anterior cut, a posterior cut and what are called chamfer cuts. These cuts are made using a cutting block, or cutting jig, which is fastened to the distal end face of the femur. For different sizes of femur, different cutting blocks with different anterior-posterior and/or mediolateral dimensions are usually present. The dimensions required in each case are chosen according to the size of the femur as previously determined by the operating surgeon. The separate determination of the size of the femur, the subsequent choice of the appropriate cutting block, and the application of the latter to the femur may entail increased expenditure in terms of time and instruments and may be the source of potential errors.

SUMMARY

With the aim of further improving patient satisfaction, there is a fundamental need for surgical instruments that are as precise as possible, easy to use and cost effective for the implementation of kinematic alignment. The present disclosure deals with such a surgical instrument and with corresponding instrument systems.

The object of the present disclosure is to provide a surgical instrument for use in a knee joint replacement operation, which instrument overcomes or lessens the disadvantages of the prior art and in particular permits savings in terms of time and/or instrumentation.

The surgical instrument according to the present disclosure has: a cutting block with a proximally oriented block rear face which is configured to bear on a distal end face of a resected femur, and with at least one guide slot which reaches from the block rear face to a distally opposite block front face and is elongate in a mediolateral direction and is configured to receive and guide a saw blade, a reference foot which can be mounted or is mounted on the cutting block, in the region of a posterior block lower face of the cutting block, and has an anteriorly oriented foot upper face which, in a mounted state of the reference foot, protrudes proximally beyond the block rear face and is configured to bear on posterior condyles of the femur, and a probe which can be mounted or is mounted on the cutting block, in the region of a block upper face lying anteriorly opposite the block lower face, and has a probe tip which, in a mounted state of the probe, protrudes proximally beyond the block rear face and is configured to bear on an anterior face of the femur. By virtue of the solution according to the present disclosure, it is possible to dispense with a separate size measurement and/or size check and with a separate measurement instrument usually required for this purpose. In this way, it is possible to save time, reduce the outlay on instruments and thus reduce associated costs. The surgical instrument according to the present disclosure permits, on the one hand, the necessary size measurement and/or size check of the femur. The reference foot and the probe are present in particular for this purpose and are mounted or mountable on the cutting block. On the other hand, the surgical instrument according to the present disclosure permits guiding of the cuts necessary for the further resection of the femur. For this purpose, the cutting block is present and has the aforementioned at least one guide slot for receiving and guiding the saw blade. In one embodiment, the reference foot and the probe are each mounted releasably on the cutting block. In a further embodiment, the reference foot and the probe are each connected permanently to the cutting block. The cutting block can also be referred to as a sawing block or cutting jig. In a preferred embodiment, the cutting block has a plurality of guide slots, preferably an anterior guide slot, a posterior guide slot and two chamfer guide slots, such that it can also be referred to as a four-in-one cutting block. The block rear face serves for distal referencing. During the use of the surgical instrument, the block rear face contacts the distal end face of the resected femur. The foot upper face serves for posterior referencing. During the use of the surgical instrument, the foot upper face contacts the posterior condyles of the femur. The probe, more precisely its probe tip, serves for anterior referencing. During the use of the surgical instrument, the probe tip contacts the aforementioned anterior face of the femur. The probe can also be designated as a stylus. In one embodiment, the probe tip is movable relative to the cutting block, preferably linearly movable in the proximodistal direction and/or pivotable about an anteroposterior pivot axis. In a further embodiment, the probe tip is not movable relative to the cutting block.

The position, orientation and/or direction designations used in this description relate to the body of a patient, in particular the femur of the patient, and to this extent they are to be understood in accordance with their usual anatomical meaning. Consequently, "anterior" denotes front or lying to the front, "posterior" denotes rear or lying to the rear, "medial" denotes inner or lying to the inside, "lateral" denotes outer or lying to the outside, "proximal" denotes towards the centre of the body, and "distal" denotes away from the centre of the body. Furthermore, "proximodistal" denotes along, preferably parallel to, a proximal-distal axis, "anteroposterior" denotes along, preferably parallel to, an anterior-posterior axis, and "mediolateral" denotes along, preferably parallel to, a medial-lateral axis. The aforementioned axes are orthogonal to one another and can of course be understood in relation to X, Y and Z axes not associated with the anatomy of the patient. For example, the proximal-distal axis can be designated alternatively as the X axis. The medial-lateral axis can be designated as the Y axis. The anterior-posterior axis can be designated as the Z axis. For the sake of better illustration and simplicity of the designations, the aforementioned anatomical position, orientation and/or direction designations are primarily used in the following. Moreover, designations such as the "rear face" of a component or of a portion of the surgical instrument, for example of the cutting block, are used with respect to a proximally oriented viewing direction. By contrast, designations such as "front face" are used with respect to a distally oriented viewing direction.

In one embodiment of the present disclosure, the cutting block has a posteriorly arranged first fastening recess, the reference foot has a complementary fastening element, and the first fastening recess and the fastening element are releasably connectable or connected to each other with form-fit and/or force-fit engagement. In different embodiments, the first fastening recess and the fastening element form different types of joining connections. In one embodiment, there is a releasable plug connection. In other embodiments, there is a latching, clamping and/or snap-fit connection or the like. A screw connection is moreover conceivable. The releasable connection between the cutting block and the reference foot means that the latter can be released and removed from the cutting block after the size check has been made. Thereafter, suitable cuts can be made using the cutting block.

In a further embodiment of the present disclosure, the first fastening recess is a receiving slot which reaches from the block rear face to the block front face and which is straight and elongate in a mediolateral direction, and the fastening element is a flat plate-shaped plug element which is configured to be plugged with form-fit and/or force-fit engagement into the receiving slot. To fasten the reference foot, the plug element is plugged, starting from the block front face, in the proximal direction into the receiving slot. The plug element has a geometry complementing the receiving slot, and vice versa. In the plugged-in state, the plug element is held in the receiving slot with form-fit and/or force-fit engagement. Simple yet robust fastening of the reference foot is thereby achieved.

In a further embodiment of the present disclosure, the plug element has at least one separating gap which extends in a anteroposterior direction and which is substantially U-shaped in longitudinal extent so as to form an elastically resiliently movable spring tongue portion, wherein the spring tongue portion, in the mounted state of the reference foot, is biased against an inner wall of the receiving slot. In this way, increased friction is obtained between the reference foot, more precisely the spring tongue portion, and the receiving slot, more precisely the inner wall of the latter. This leads to improved fastening of the reference foot. On account of the substantially U-shaped longitudinal extent of the separating gap, the spring tongue portion is tongue-shaped and/or has a tongue shape. The separating gap extends in the anteroposterior direction and therefore, starting from an anteriorly oriented upper face of the plug element, reaches all the way to a posteriorly oriented lower face of the plug element. In one embodiment, the spring tongue portion presses against the inner wall of the receiving slot from the upper face of the plug element (anteriorly) and, in a further embodiment, from the lower face of the plug element (posteriorly).

In a further embodiment of the present disclosure, the receiving slot has two separate slot portions which are separated from each other in a mediolateral direction by a web, and the plug element has two separate plug portions which are separated from each other in the mediolateral direction by a gap. In the fastened state of the reference foot, the web enters the gap and leads to further improved fastening. This in particular in the mediolateral direction. In this embodiment of the present disclosure, it is also possible to refer to a first slot portion and a second slot portion and, accordingly, a first plug portion and a second plug portion.

In a further embodiment of the present disclosure, the receiving slot, in a non-mounted state of the reference foot, is configured to receive and guide the saw blade and forms a posterior guide slot of the cutting block. This is a particularly preferred embodiment of the present disclosure. In this embodiment, the receiving slot has a particularly advantageous multiple function. On the one hand, the receiving slot serves to receive the plug element for the purpose of releasably fastening the reference foot to the cutting block. On the other hand, the receiving slot serves as a guide slot for the saw blade. A particularly simple and compact structure of the cutting block can be achieved in this way.

In a further embodiment of the present disclosure, the first fastening recess is a receiving pocket sunk proximally into the block front face, and the fastening element is configured to form a latching and/or clamping connection with the receiving pocket. Accordingly, the fastening element is a latching element in one embodiment and a clamping element in another embodiment.

In a further embodiment of the present disclosure, the reference foot forms a flat plate-shaped extension which is spaced apart posteriorly from the fastening element and whose upper face forms the foot upper face. In the fastened state of the reference foot, the extension is arranged below the block lower face, i.e., spaced posteriorly apart from the latter. For this purpose, the extension is spaced apart posteriorly from the fastening element. The upper face of the extension is oriented anteriorly and is configured to bear on the posterior condyles of the femur. The extension protrudes in the proximal direction beyond the block rear face. In one embodiment, the extension has two separate extension portions, which are separated from each other in the mediolateral direction by a web. In this embodiment, reference can also be made to a first extension portion and a second extension portion or alternatively a medial extension portion and a lateral extension portion. The medial extension portion is provided for referencing on the medial posterior condyle. Accordingly, the lateral extension portion is provided for referencing on the lateral posterior condyle.

In a further embodiment of the present disclosure, the reference foot has a distally arranged grip portion from which the fastening element and/or the extension protrudes in the proximal direction, wherein the grip portion has a laterally oriented first grip surface, a medially oriented second grip surface and a proximally oriented stop face. The grip portion permits ergonomic manual handling of the reference foot by the operating surgeon. For this purpose, the grip portion is arranged distally on the reference foot. In the fastened state of the reference foot, the grip portion is thus arranged easily accessibly on the block front face. The grip portion can be gripped between the fingers of one hand and for this purpose has the two grip surfaces. The laterally oriented first grip surface is arranged laterally and can thus also be designated as the lateral grip surface. The medially oriented second grip surface is arranged medially and can therefore also be designated as the medial grip surface. The proximally oriented stop face is particularly advantageous in connection with embodiments in which the fastening element of the reference foot is designed as a plate-shaped plug element. In this case, the proximally oriented stop face limits the depth by which the plug element is plugged into the receiving slot.

In a further embodiment of the present disclosure, the cutting block has an anteriorly arranged second fastening recess, the probe has a complementary fastening element, and the second fastening recess and the fastening element of the probe are releasably connectable or connected to each other with form-fit and/or force-fit engagement. In this way, after the size measurement and/or size check has been carried out, the probe can be easily released and removed from the cutting block. Thereafter, the further resection of the distal femur can take place using the cutting block. In different embodiments, the second fastening recess and the fastening element of the probe form different joining connections, for example a plug connection, latching connection, clamping connection and/or snap-fit connection. A screw connection is moreover conceivable.

In a further embodiment of the present disclosure, the second fastening recess is designed as a constituent part of a universal fastening system and is configured for connection to further instrument components, preferably a surgical navigation device. The further instrument component therefore likewise has a complementary fastening element. The universal fastening system allows the option of different instrument components being fastened to and released from the cutting block. In particular, the probe and alternatively at least one further instrument component, in particular the aforementioned navigation device, can be fastened releasably to the cutting block.

In a further embodiment of the present disclosure, the second fastening recess has a latch recess which is sunk posteriorly into the block upper face, is elongate in the mediolateral direction and is open at a medial or lateral end, and the fastening element of the probe has a complementary latch portion which interacts with the latch recess of the cutting block to form a releasable snap-fit connection. The latch recess is elongate in the mediolateral direction and, in one embodiment, is open in the direction of a medial block outer face and, in a further embodiment, is open in the direction of a lateral block outer face. Accordingly, the complementary latch portion can be pushed in the lateral direction or in the medial direction into the latch recess and can be connected thereto in order to form the snap-fit connection. The latch recess is moreover sunk into the block upper face and to this extent open in the anterior direction. In this way, the snap-fit connection is particularly easy for the operating surgeon to see. It is thus possible to easily identify whether the snap-fit connection has or has not formed as required.

In a further embodiment of the present disclosure, the second fastening recess has a plug recess which extends mediolaterally into a block outer face of the cutting block, and the fastening element of the probe has a complementary plug portion which interacts with the plug recess to form a releasable plug connection. Preferably, the plug recess has a cylindrical, preferably circular cylindrical, cross-sectional shape. The same applies, mutatis mutandis, regarding the cross-sectional shape of the complementary plug portion of the probe. The plug portion can also be designated as a pin, bolt and/or peg. Accordingly, the plug recess can also be designated as a bore, pin recess, peg recess and/or bolt recess. In one embodiment, the plug recess, starting from the lateral block outer face of the cutting block, extends in the medial direction into the latter. In a further embodiment, by contrast, the plug recess, starting from a medial block outer face, extends in the lateral direction into the latter. This embodiment of the present disclosure is particularly advantageous in combination with embodiments in which the second fastening recess additionally has a latch recess. In this case, the plug recess serves for improved fastening. The plug recess is preferably arranged on the cutting block at a location spaced apart posteriorly from the latch recess.

In a further embodiment of the present disclosure, a plurality of different compensation elements with different anteroposterior thickness are present, wherein the different compensation elements are each configured to be mountable, preferably pluggable, onto the foot upper face and to compensate for different degrees of wear of the posterior condyles. The different compensation elements serve to correct the orientation of the cutting block with respect to the longitudinal axis of the femur. In other words, a rotation of the cutting block about a proximodistal axis can be adjusted by means of the different compensation elements. The kinematic alignment approach generally provides a so-called 0° orientation. In order to ensure a 0° orientation, any wear of the posterior condyles has to be compensated. The wear can of course vary greatly in extent. Accordingly, a plurality of differently dimensioned, more precisely differently thick, compensation elements are present. The greater the degree of wear, the thicker the required compensation element. The different compensation elements are each mountable on the foot upper face and are configured for direct contact with the posterior condyles. Preferably, the plurality of different compensation elements comprise lateral compensation elements for contacting the lateral posterior condyle and medial compensation elements for contacting the medial posterior condyle.

The present disclosure further relates to a surgical instrument system for use in a knee joint replacement operation, having at least one surgical instrument according to the above description, wherein the reference foot and the probe are each mounted releasably on the cutting block, and having further different cutting blocks which differ from one another in terms of at least one dimension, in particular an anteroposterior and/or mediolateral dimension, wherein the reference foot and the probe are each mountable on each of the further different cutting blocks. During the use of the surgical instrument system, the appropriate cutting block is chosen, for example, on the basis of a pre-operative examination, X-ray images or the like. After the preliminary selection of the cutting block from the plurality of different cutting blocks, the reference foot and the probe can be mounted on the cutting block. Here, the reference foot and the probe serve in the first instance for checking the preselection of the size of the cutting block. For this purpose, the foot upper face is placed in the above-described manner onto the posterior condyles of the femur. The block rear face is placed onto the distal end face of the resected femur. The actual check is then made by means of the probe tip. If, with the foot upper face and the block rear face accordingly positioned, the probe tip at the same time contacts an anterior face of the femur, in the region where the anterior shield of the implanted femoral component later comes to lie, it is possible to infer that the correct size of cutting block has been preselected.

In a further embodiment of the present disclosure, the reference foot and the probe are each mounted permanently on the cutting block. In this embodiment, the corresponding connection between reference foot and cutting block and between probe and cutting block is not releasable, at least not during the operation. For example, a non-releasable joining connection can be present in each case.

The present disclosure further relates to a surgical instrument system for use in a knee joint replacement operation, having a plurality of different surgical instruments according to the preceding embodiment, wherein the plurality of different surgical instruments differ from one another in terms of at least one dimension, in particular an anteroposterior and/or mediolateral dimension, of the respective cutting block. In this surgical instrument system, each of the plurality of different surgical instruments has a respective cutting block, a reference foot and a probe. The reference feet and the probes of the different surgical instruments are each mounted permanently and/or non-releasably on the respective cutting block.

BRIEF DESCRIPTION OF THE DRAWINGS

Further advantages and features of the present disclosure follow from the claims and from the following description of preferred illustrative embodiments of the present disclosure, which are explained with reference to the drawings.

DETAILED DESCRIPTION

According to FIGS. 1-6, a surgical instrument 1 for use in a knee joint replacement operation is provided and has a cutting block 100, a reference foot 200 and a probe 300.

The cutting block 100 has a proximally oriented block rear face 101, a distally opposite block front face 102, an anterior block upper face 103, a posterior block lower face 104, a lateral block outer face 105 and a medial block outer face 106. The block rear face 101 is configured to bear on a distal end face S of a resected femur F (see FIGS. 5 and 6). A normal direction of the block rear face 101 is oriented parallel to the proximodistal axis indicated in FIGS. 1 and 2 and points in the proximal direction. The cutting block 100 moreover has at least one guide slot 107. In the present case, a plurality of guide slots are provided, namely said guide slot 107, which can also be designated as the anterior guide slot 107, a posterior guide slot 108, and chamfer guide slots 109, 110. The guide slots 107, 108, 109, 110 each extend all the way from the block front face 102 to the block rear face 101. Moreover, the guide slots 107, 108, 109, 110 are each elongate in a mediolateral direction, i.e., parallel to the mediolateral axis indicated in FIGS. 1 and 2. The guide slots 107, 108, 109, 110 are each configured to receive and guide a saw blade (not shown in the drawing).

The reference foot 200 is mounted on the cutting block in the region of the posterior block lower face 104 and has an anteriorly oriented foot upper face 201. A surface normal (not shown) of the foot upper face 201 is therefore parallel to the anteroposterior axis indicated in FIGS. 1 and 2 and points in the anterior direction. The foot upper face 201 protrudes beyond the block rear face 101 in the proximal direction and is configured to bear on posterior condyles KL, KM of the femur F (see FIGS. 5 and 6). In the present embodiment, the reference foot 200 is connected releasably to the cutting block 100 in a manner to be described in detail.

The probe 300 is mounted on the cutting block 100 in the region of the block upper face 103 and has a probe tip 301. The probe tip 301 protrudes in the proximal direction beyond the block rear face 101 and is configured to bear on an anterior face A of the femur F (see FIGS. 5 and 6). In the present embodiment, the probe 300 is connected releasably to the cutting block 100 in a manner to be described in detail.

The surgical instrument 1 serves multiple purposes. On the one hand, the surgical instrument 1 can be used for a size measurement and/or size check on the distally resected femur F. On the other hand, the surgical instrument serves to guide the aforementioned saw blade during the resection of the femur.

For a size measurement and/or size check, the block rear face 101 is brought into contact with the end face S. At the same time, the foot upper face 201 is brought into contact with the posterior condyles KL, KM. In this way, the surgical instrument is oriented with respect to the anteroposterior axis and the proximodistal axis of the femur F. The actual size measurement and/or size check is carried out by means of the probe 300 and according to whether its probe tip 301 contacts the anterior face A of the femur F in a given orientation of the surgical instrument 1 on the end face S and the posterior condyles KL, KM.

After the size measurement and/or size check has taken place, the cutting block 100 is fixed to the femur in a manner known to those skilled in the art, for example by means of suitable pins, screws or the like. These can be introduced into fastening openings 111 provided for this purpose in the cutting block (see FIGS. 7 and 8). After the cutting block 100 has been fastened to the femur, the further resection of the femur F takes place. For this purpose, the saw blade is guided through the guide slots 107, 108, 109, 110 in a manner known to those skilled in the art, and the femur is accordingly resected. In the embodiment shown here, both the reference foot 200 and the probe 300 are released from the cutting block 100 and removed before the resection takes place.

In the embodiment shown, the cutting bock 100 and the reference foot 200 are connected to each other by means of a releasable force-fit and/or form-fit joining connection. For this purpose, the cutting block 100 has a posteriorly arranged first fastening recess 112 (see FIGS. 7 and 8). The reference foot 200 has a fastening element 202 (see FIGS. 9 and 10) that complements the first fastening recess 112.

Figure 1:
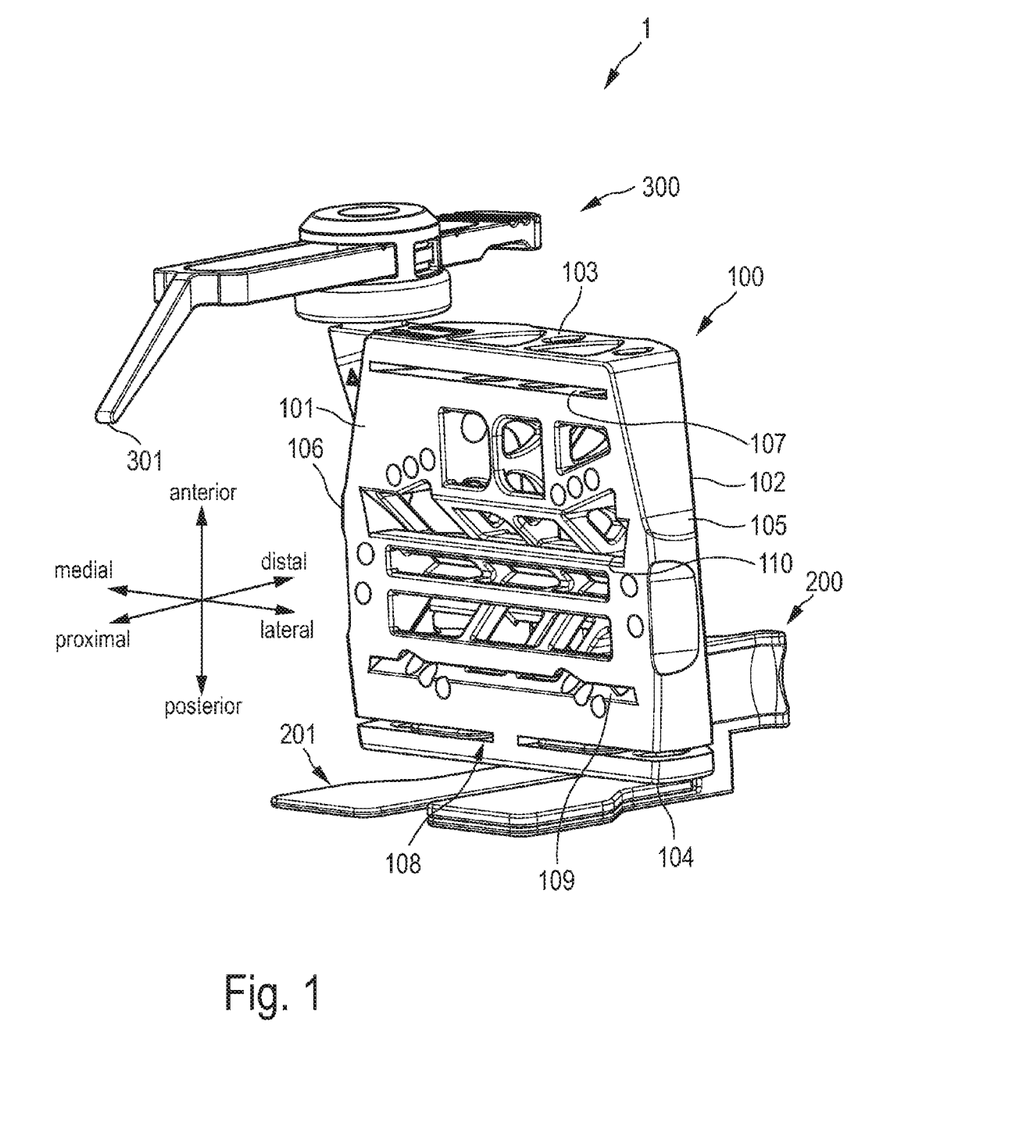
FIG. 1 shows a schematic perspective view of an embodiment of a surgical instrument according to the present disclosure with a cutting block, a reference foot and a probe.
Figure 2:
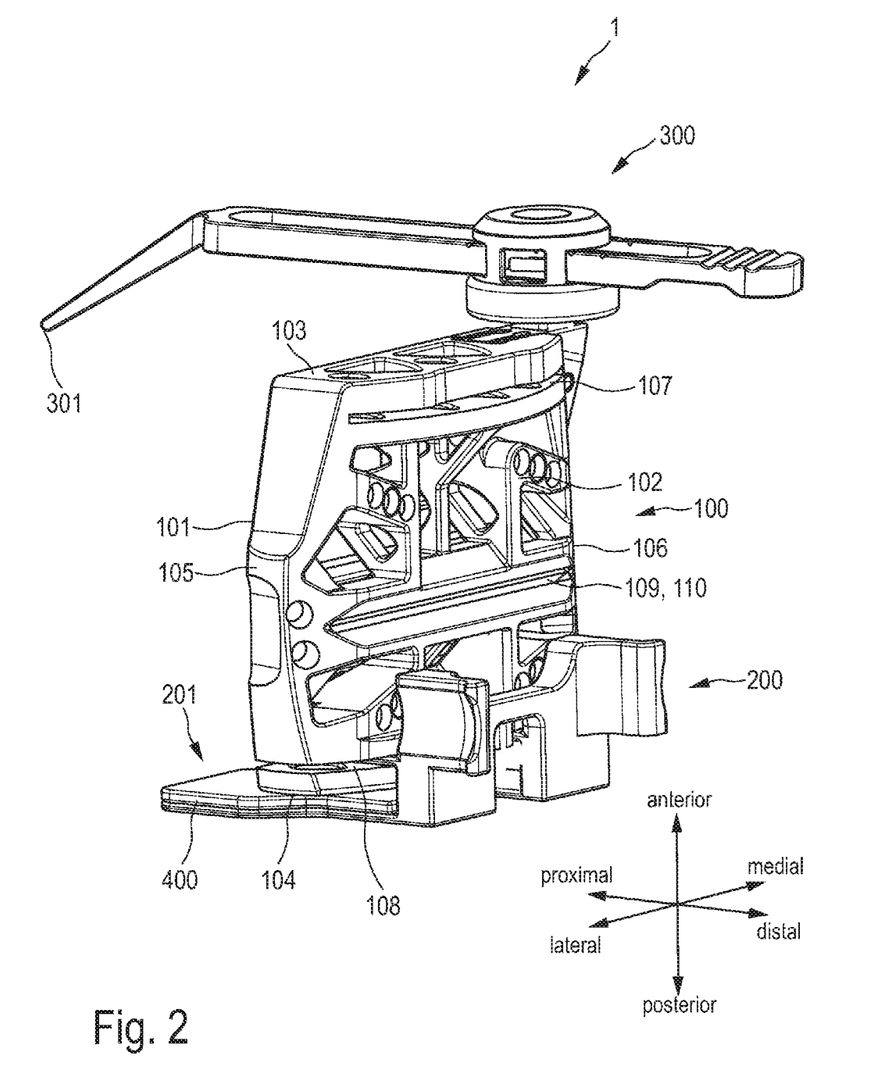
FIG. 2 shows a further schematic perspective view of the surgical instrument according to FIG. 1.
Figure 3:
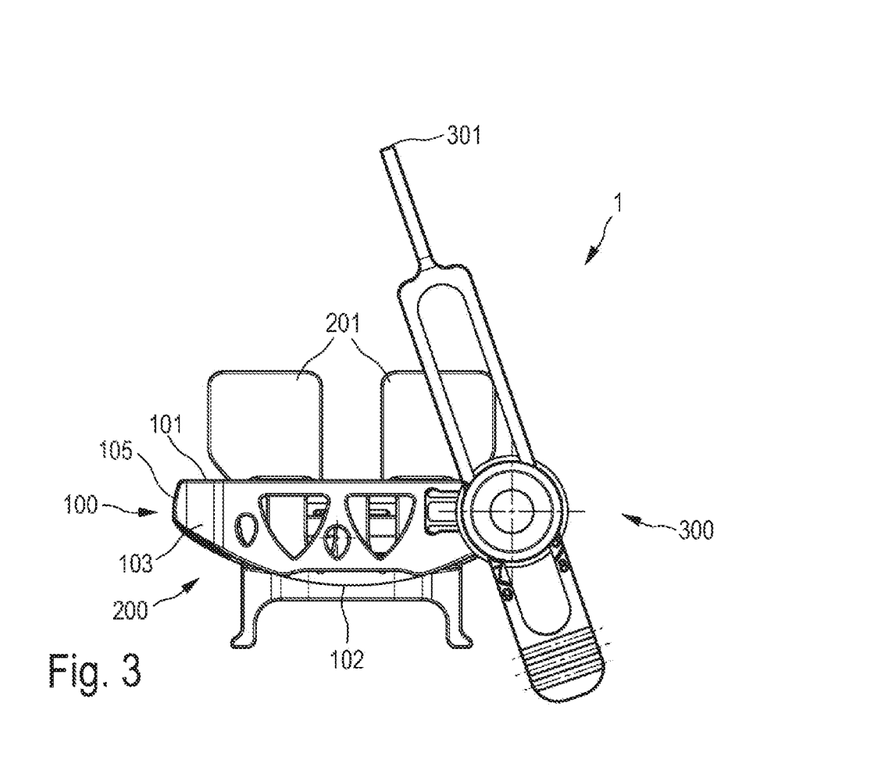
FIG. 3 shows the surgical instrument according to FIG. 1 in a schematic plan view.
Figure 4:
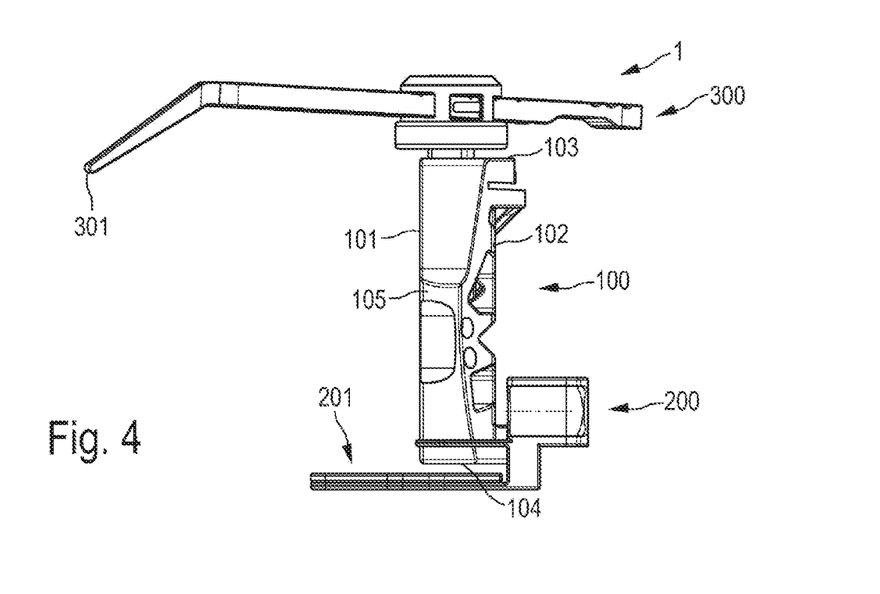
FIG. 4 shows the surgical instrument according to FIG. 1 in a schematic side view.
Figure 5:
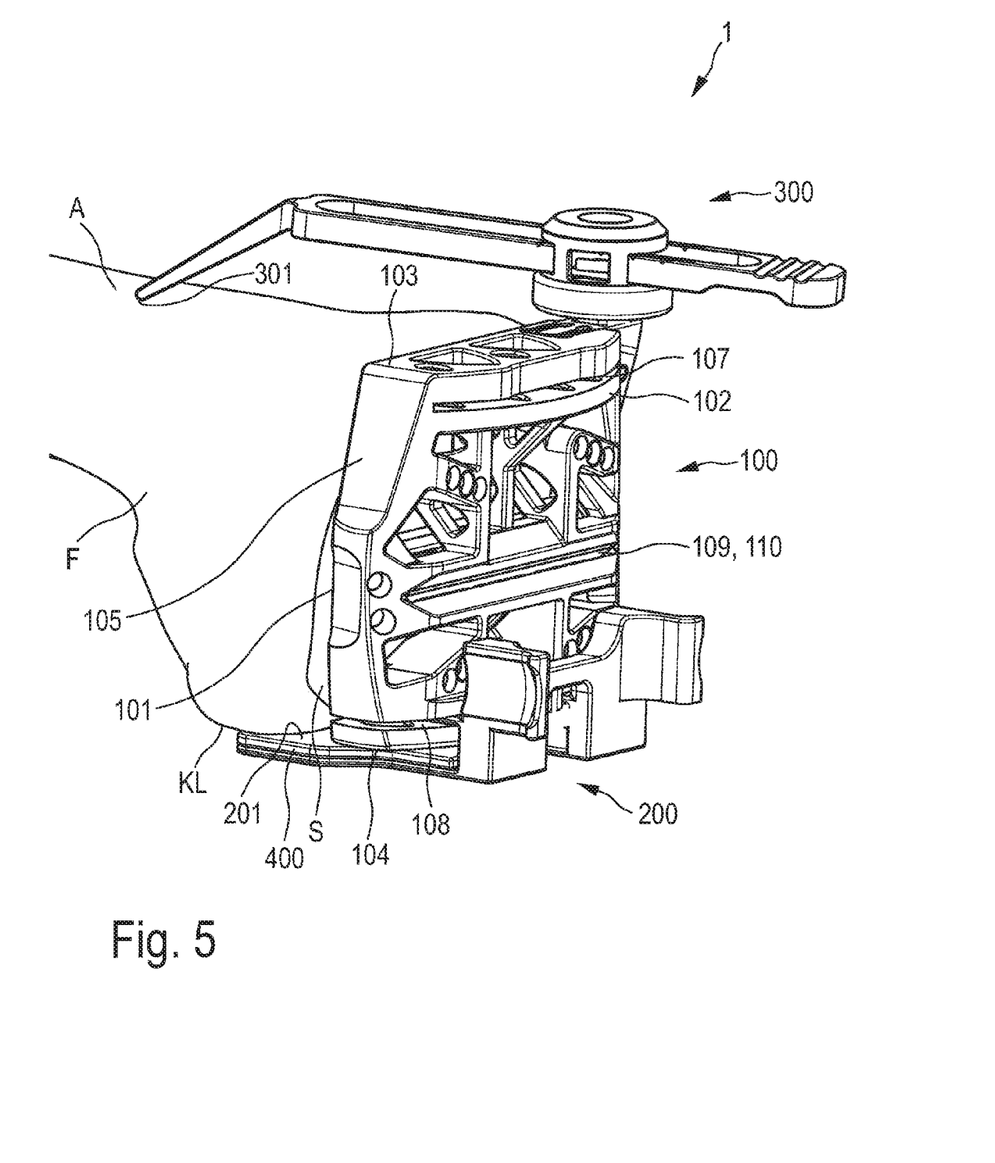
FIG. 5 shows a schematic perspective view of an example of an intraoperative situation in which the surgical instrument according to FIG. 1 is arranged on a distal femur.
Figure 6:
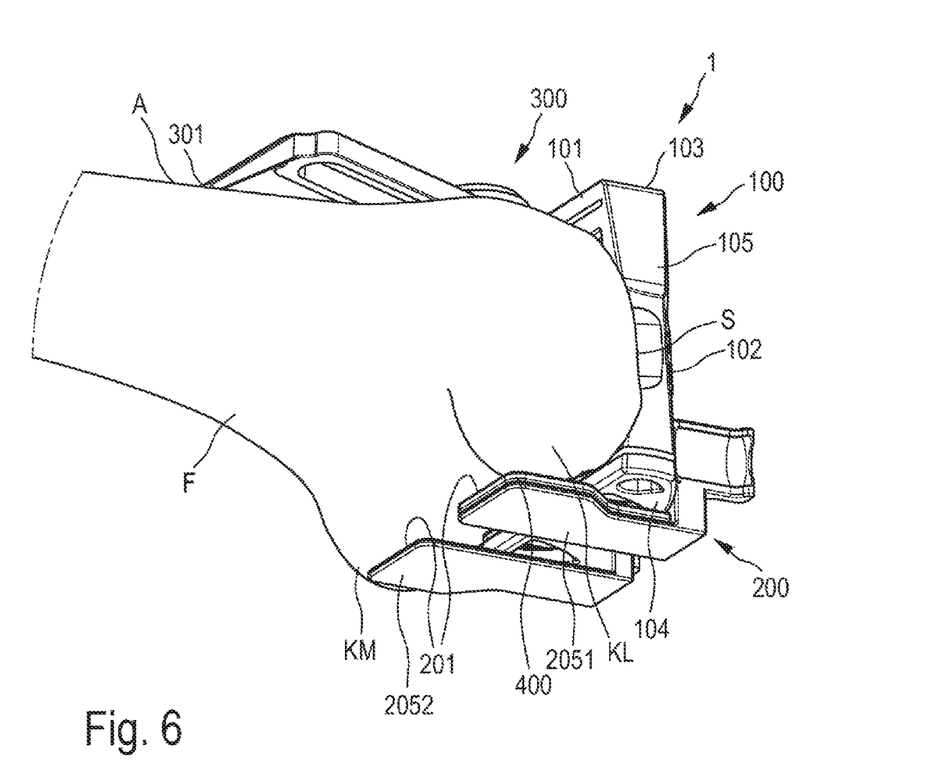
FIG. 6 shows the intraoperative situation according to FIG. 5 in a further schematic perspective view.
Figure 7:
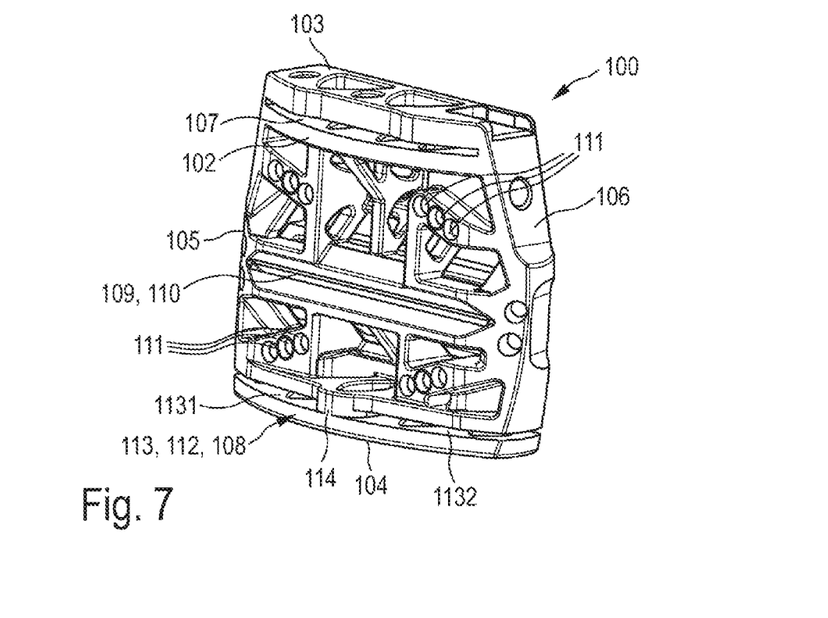
FIG. 7 shows the cutting block of the surgical instrument according to FIG. 1 a schematic perspective view, seen in the direction of a block front face.
Figure 8:
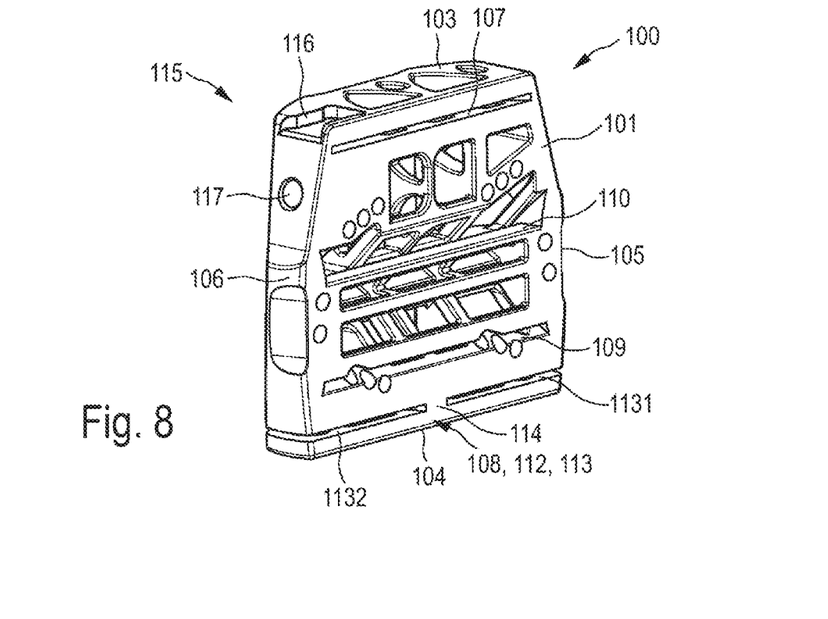
FIG. 8 shows the cutting block of the surgical instrument according to FIG. 1 in a schematic perspective view, seen in the direction of a block rear face.

The first fastening recess 112 is arranged in the region of the block lower face 104. In the embodiment shown, the first fastening recess 112 is a receiving slot 113 which reaches from the block rear face 101 to the block front face 102 and is straight and elongate in the mediolateral direction. In the embodiment shown, the receiving slot 113 has two separate slot portions 1131, 1132, which can also be designated as medial slot portion 1132 and lateral slot portion 1131. The two slot portions 1131, 1132 are separated from each other in the mediolateral direction by a web 114. The lateral slot portion 1131 is open in the lateral direction at its end opposite the web 114. The medial slot portion 1132 is open in the medial direction at its end opposite the web 114.

In the embodiment shown, the receiving slot 113 has a particularly advantageous multiple function. On the one hand, the receiving slot serves to receive the complementary fastening element 202 with form-fit and/or force-fit engagement. On the other hand, the receiving slot 113, in a state with the reference foot 200 not fastened to the cutting block 100, serves as the posterior guide slot 108. To put it another way, the posterior guide slot 108 serves at the same time as the receiving slot 113.

The complementary fastening element 202 (see FIGS. 9 and 10) is designed to match the receiving slot 113 and in the present case is a flat plate-shaped plug element 203 which is configured to be plugged with form-fit and/or force-fit engagement into the receiving slot 113. The plug element 203 is in the present case flat with respect to the mediolateral axis and with respect to the proximodistal axis. Corresponding to the in the broadest sense two-part receiving slot 113, the plug element 203 has two separate plug portions 2031, 2032. These can also be designated as medial plug portion 2032 and lateral plug portion 2031. The two plug portions 2031, 2032 are separated from each other in the mediolateral direction by a gap 204. A mediolateral extent of the gap 204 is greater here than the corresponding extent of the web 114.

Figure 9:
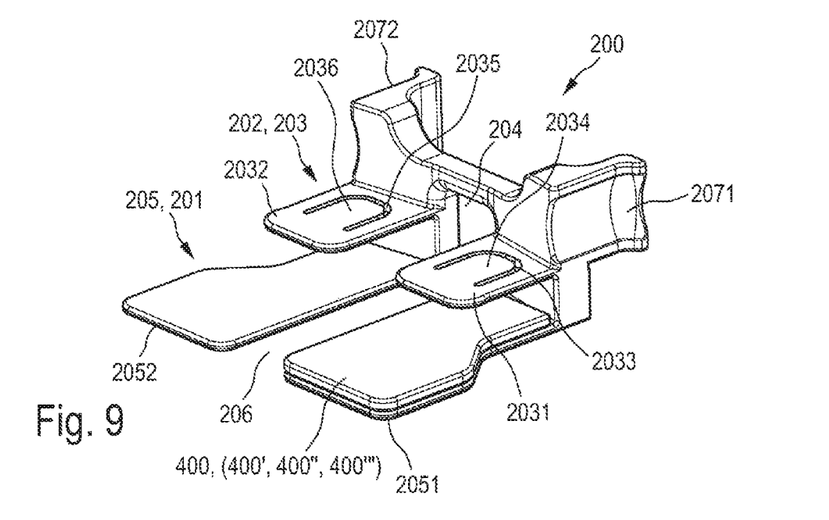
FIG. 9 shows a schematic perspective view of a reference foot of the surgical instrument according to FIG. 1.
Figure 10:
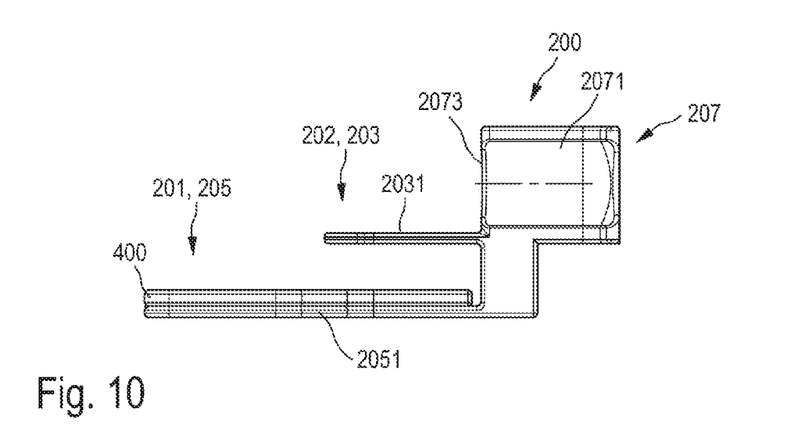
FIG. 10 shows a schematic side view of the reference foot according to FIG. 9.

To fasten the reference foot 200 to the cutting block 100, the plug element 203 is plugged proximally into the receiving slot 113. In the process, the lateral plug portion 2031 is inserted into the lateral slot portion 1131 and the medial plug portion 2032 is inserted into the medial slot portion 1132.

In the embodiment shown, the plug element 203 has at least one separating gap 2033 which extends in the anteroposterior direction and which is substantially U-shaped in longitudinal extent so as to form an elastically resiliently movable spring tongue portion 2034. The spring tongue portion 2034, in the plugged-in state of the plug element 203, bears on an inner wall (not shown in detail) of the receiving slot 113 under the loading of a spring force. The spring tongue portion 2034 presses anteriorly or posteriorly against said inner wall. This leads to increased friction and therefore to an improved and particularly reliable fastening of the reference foot 200. In the embodiment shown, the separating gap 2033 and the spring tongue portion 2034 are arranged on the lateral plug portion 2031, such that they can also be referred to as a lateral separating gap 2033 and a lateral spring tongue portion 2034. In the present case, the medial plug portion 2032 has a corresponding design with a (medial) separating gap 2035 and a (medial) spring tongue portion 2036.

In the embodiment shown, the foot upper face 201 is formed on a flat plate-shaped extension 205. To put it another way, the upper face (not described in detail) of the extension 205 forms the foot upper face 201. The extension 205 is flat with respect to the mediolateral axis and with respect to the proximodistal axis and protrudes at least in part in the proximal direction beyond the block rear face 101. In the present case, the extension 205 is oriented plane-parallel to the fastening element 203. The extension 205 is spaced apart anteriorly from the fastening element 203. In the fastened state of the reference foot 200, the extension 205 engages below the block lower face 104 (see FIG. 4 in particular).

The extension 205 has a lateral extension portion 2051 and a medial extension portion 2052. The two extension portions 2051, 2052 are separated from each other in the mediolateral direction by a gap 206. The lateral extension portion 2051 is provided for contact with the lateral posterior condyle KL. Accordingly, the medial extension portion 2052 is provided for contact with the medial posterior condyle KM.

To compensate for any wear of the posterior condyles Kl, KM, the surgical instrument 1 in the embodiment shown also has a plurality of compensation elements. Only one compensation element 400 of said plurality of compensation elements is shown in the present drawings. The different compensation elements differ in terms of their anteroposterior thickness and are each configured to be mountable on the foot upper face 201. In the present case, the compensation element 400 is mounted on the lateral extension portion 2051. For this purpose, different joining connections between the compensation element 400 (the plurality of different compensation elements) and the foot upper face 201 are conceivable in different embodiments. In the present case, the compensation element 400 is plugged onto the lateral extension portion 2051 in a manner not shown in any detail. By mounting the compensation element 400 on the lateral extension portion 2051, any wear of the lateral posterior condyle KL can be compensated since, despite said wear, it is possible to ensure that the surgical instrument 1 is oriented in rotation about the proximodistal axis in a way that meets requirements and accords with the kinematic alignment concept.

To illustrate that the surgical instrument 1 has a plurality of different compensation elements, the compensation element 400 in FIG. 9 is designated by further reference signs 400', 400", 400'" placed between parentheses. These reference signs relate to a first compensation element 400', second compensation element 400" and third compensation element 400'", which are not shown separately in the drawing. The anteroposterior thickness of the first compensation element 400' is less than that of the second compensation element 400" and of the third compensation element 400'". The anteroposterior thickness of the second compensation element 400" is greater than that of the first compensation element 400' and less than that of the third compensation element 400'". The anteroposterior thickness of the third compensation element 400'" is greater than that of the first compensation element 400' and of the second compensation element 400".

In the embodiment shown, the reference foot 200 moreover has a grip portion 207. The grip portion 207 is arranged distally on the reference foot 200 and has a lateral grip surface 2071, a medial grip surface 2072 and a stop surface 2073. The grip portion 207 serves for simplified manual handling of the reference foot 200. The fastening element 202 protrudes in the proximal direction from the grip portion 207. The extension 205 protrudes in the proximal direction from the grip portion 207. The lateral grip surface 2071 is oriented substantially laterally, such that the corresponding surface normal is approximately parallel to the mediolateral axis and points in the lateral direction. The same applies mutatis mutandis to the medial grip surface 2072. To fasten and release the reference foot, the grip portion 207 is gripped between the fingers of one hand, for example with the thumb placed on the lateral grip surface 2071 and the index finger placed on the medial grip surface 2072. The stop surface 2073 is oriented proximally and serves primarily to limit the depth by which the plug element 203 is plugged into the receiving slot 113. In the plugged-in state, the stop surface 2073 contacts the block front face 102.

To releasably connect the probe 300 to the cutting block 100, the latter has an anteriorly arranged second fastening recess 115. The probe 300 has a fastening element 302 complementing the second fastening recess 115. The second fastening recess 115 and the fastening element 302 of the probe 300 are connectable or connected to each other with form-fit and/or force-fit engagement.

As is shown in particular in FIGS. 7 and 8, the second fastening recess, here 115, has a latch recess 116 and a plug recess 117.

The latch recess 116 is sunk in the posterior direction into the block upper face 103 and, starting from the medial block outer face 106, extends mediolaterally into the cutting block 100. The latch recess 116 is here open in the anterior direction (to the top). Thus, the latch recess 116 is in the broadest sense of pocket-shaped design.

The plug recess 117, starting from the medial block outer face 106, is introduced in the lateral direction into the cutting block 100. In the present case, the plug recess 117 has a circular cylindrical cross section and can be designated as a bore. In an embodiment not shown in the drawing, both the latch recess 116 and the plug recess 117 are arranged laterally on the cutting block 100. It is moreover conceivable that the cutting block has a second fastening recess both medially and laterally. The plug recess 117 is spaced apart posteriorly from the latch recess 116.

Figure 11:
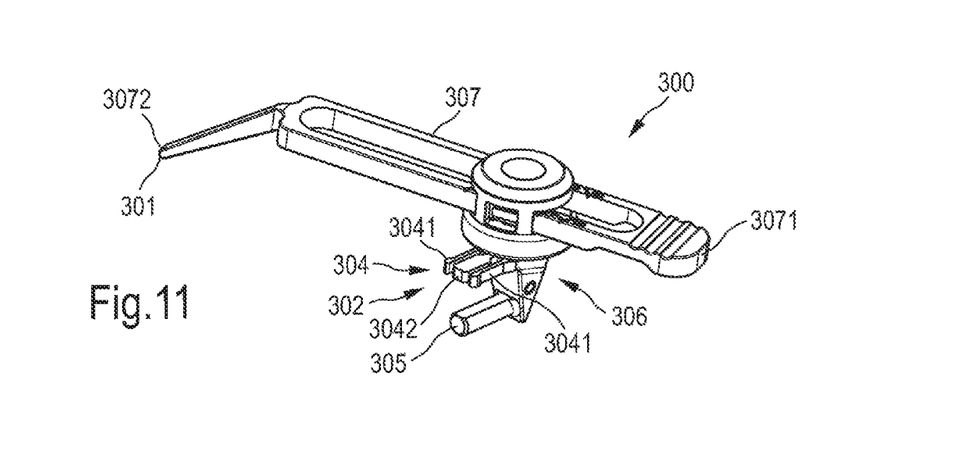
FIG. 11 shows a schematic perspective view of a probe of the surgical instrument according to FIG. 1.

The complementary fastening element 302 of the probe 300 has a latch portion 304 and a plug portion 305 (see FIG. 11).

The latch portion 304 is designed to complement the latch recess 116 and in the present case has two elastic spring limbs 3041. The elastic spring limbs 3041 lie opposite each other with respect to the proximodistal axis and are elastically movable along same. With respect to the proximodistal axis between the two spring limbs 3041, the latch portion 304 has a guide pin 3042.

The plug portion 305 is designed to complement the plug recess 117 and in the present case therefore has a peg shape, pin shape and/or bolt shape. The plug portion 305 is straight and elongate in the mediolateral direction.

In the fastened state of the probe 300, the plug portion 305 is oriented coaxially to the plug recess 117 and is plugged axially into the latter. Accordingly, the latch portion 304 is latched into the latch recess 116. The two spring limbs 3041 are latched with form-fit engagement onto an inner contour (not shown in any detail) of the latch recess 116. The present design of the second fastening recess 115 and of the complementary fastening element 302 provides in particular improved torque support about the mediolateral axis. In this way, an undesired relative movement of the probe tip 301 with respect to the cutting block 100 is counteracted.

In the embodiment shown, the second fastening recess 115 is a constituent (integral) part of a universal fastening system and is configured for connection to further instrument components not shown in detail in the drawings. In this way, instead of the probe 300, a further instrument component likewise provided with a complementary fastening element can be chosen to be releasably connected to the cutting block 100. The instrument component in question is in particular a surgical navigation device or the like.

In the embodiment shown, the probe tip 301 is movable relative to the cutting block 100. For this purpose, the probe 300 in the present case has a bearing block 306 and a probe element 307 mounted movably on the latter.

Figure 12:
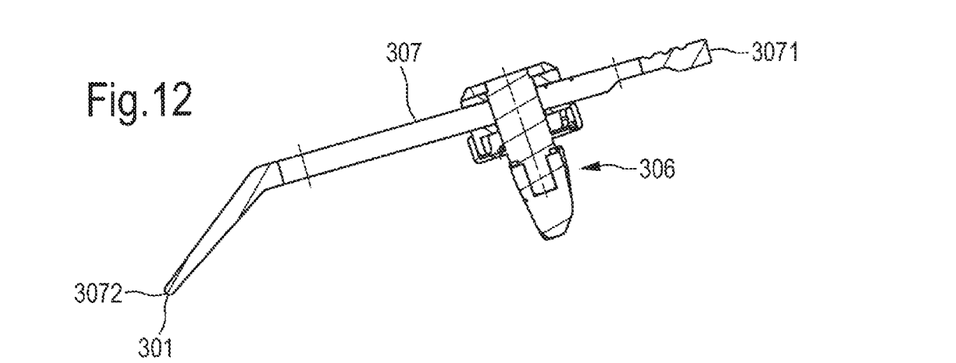
FIG. 12 shows a schematic longitudinal sectional view of the probe according to FIG. 11, along a section B-B according to FIG. 13.
Figure 13:
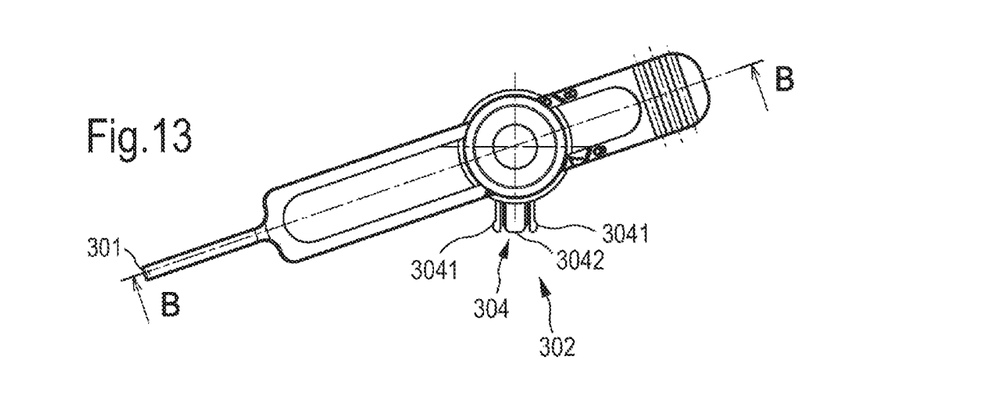
FIG. 13 shows a schematic plan view of the probe according to FIG. 11.

The probe element 307 is elongate between a first end 3071 and a second end 3072, the probe tip 301 being formed at the second end 3072. The probe element 307 is guided in its longitudinal direction relative to the bearing block 306, linearly movably on the latter. Moreover, the probe element 307 is pivotable relative to the bearing block 306 about a pivot axis. The pivot axis (not shown in any detail) is oriented parallel to the anteroposterior axis. The bearing block 306 has the complementary fastening element 302 and therefore both the latch portion 304 and the plug portion 305.

Figure 14:
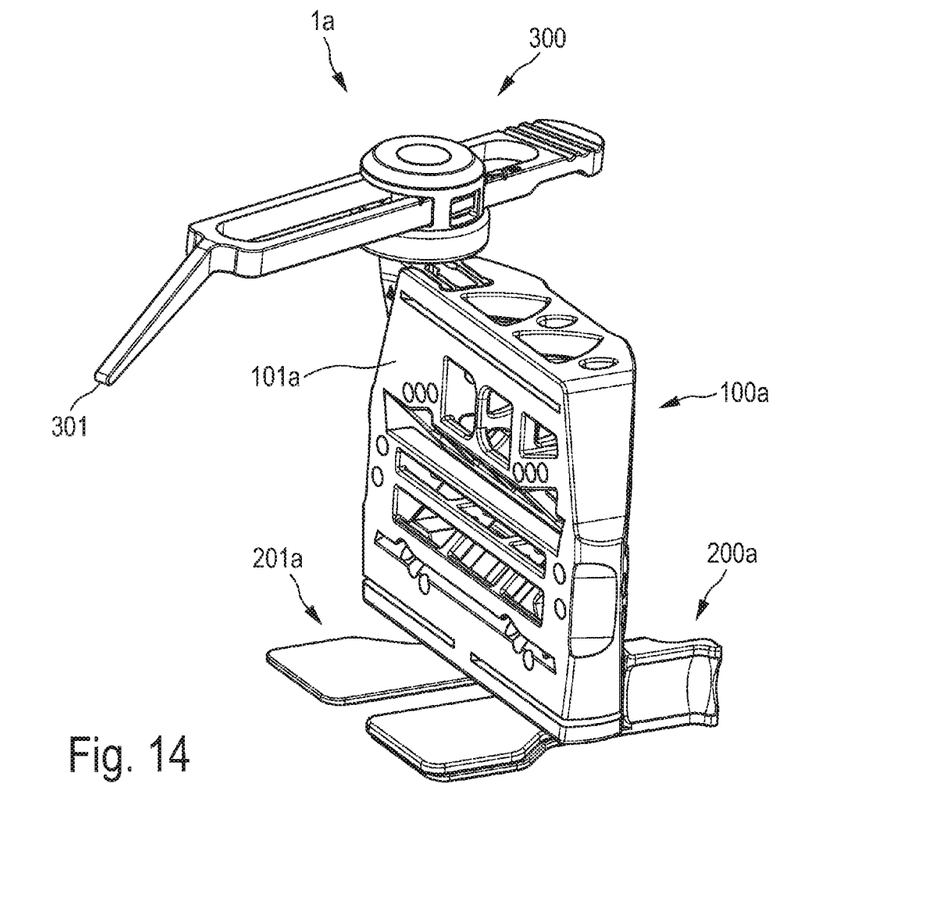
FIG. 14 shows a schematic perspective view of a further embodiment of a surgical instrument according to the disclosure.

FIG. 14 shows a further embodiment of a surgical instrument 1a according to the present disclosure. The function and the structure of the surgical instrument 1a are largely identical to the function and structure of the surgical instrument 1 according to FIGS. 1-6. To avoid repetition, only major differences of the surgical instrument 1a in relation to the surgical instrument 1 are explained below. Functionally identical structural parts and/or portions of the surgical instrument 1a are not explained separately. Instead, reference is expressly made to the disclosure of the surgical instrument 1.

The surgical instrument 1a mainly differs in terms of the different way in which the reference foot 200a is fastened to the cutting block 100a. By contrast, the probe 300 and its fastening to the cutting block 100a are identical to the probe 300 of the surgical instrument 1.

Figure 15:
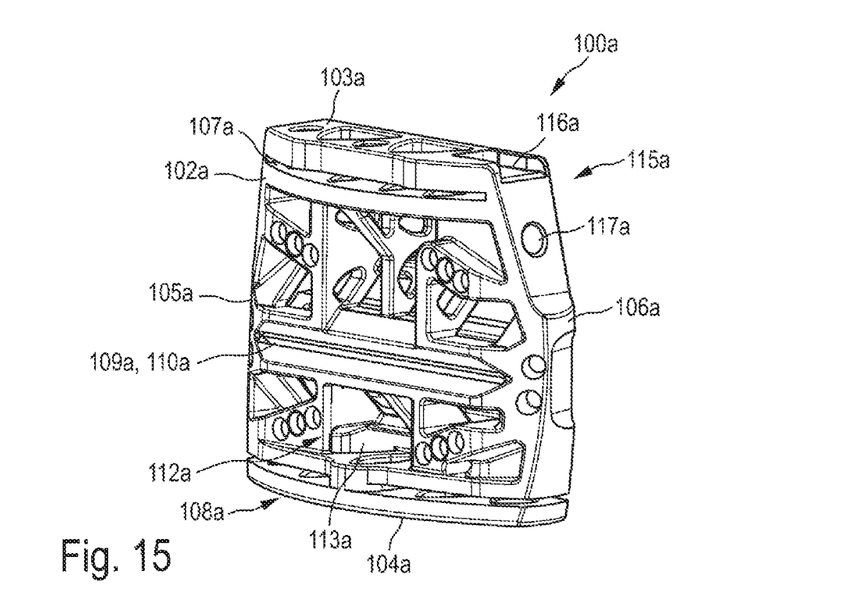
FIG. 15 shows a schematic perspective view in the direction of a block front face of the cutting block of the surgical instrument according to FIG. 14.

The cutting block 100a has a first fastening recess 112a. The latter is in the present case a receiving pocket 113a sunk proximally into the block front face 102a. The receiving pocket 113a is spaced apart anteriorly from the posterior guide slot 108a of the cutting block 100a and is arranged approximately centrally between the block outer faces 105a, 106a.

The reference foot 200a (FIG. 16) has a fastening element 202a that complements the receiving pocket 113a. The fastening element 202a is configured to establish a latching and/or clamping connection with the receiving pocket 113a. In the embodiment shown, the fastening element 202a has a wedge-shaped design and extends between a distal end 2021a and a proximal end 2022a. The fastening element 202a flattens with a wedge shape in the direction of the proximal front end 2022a.

Figure 16:
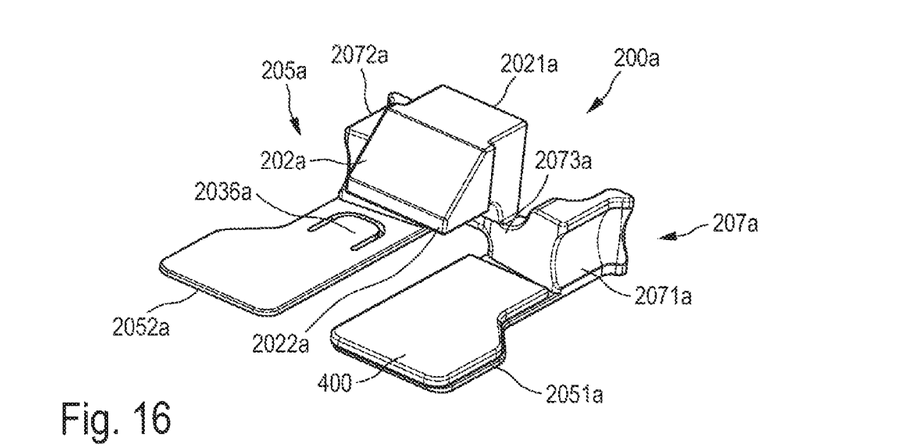
FIG. 16 shows a schematic perspective view of a reference foot of the surgical instrument according to FIG. 14.

For releasable connection to the cutting block 100a, the fastening element 202a is inserted, with the proximal end 2022a to the front, into the receiving pocket 113a. The aforementioned latching and/or clamping connection is thus obtained.

In other respects, the reference foot 200a has a structure that corresponds substantially to the reference foot 200 of the surgical instrument 1 according to FIGS. 1-13. Once again, a lateral extension portion 2051a and a medial extension portion 2052a are present. Here, the medial extension portion 2052a is provided with a spring tongue portion 2036a which, in order to frictionally support the fastening of the reference foot, presses against the block lower face 104a with loading of a spring force. To compensate for any wear of the condyles, a compensation element 400 is plugged onto the lateral extension portion 2051a, although this of course is not essential.

Figure 17:
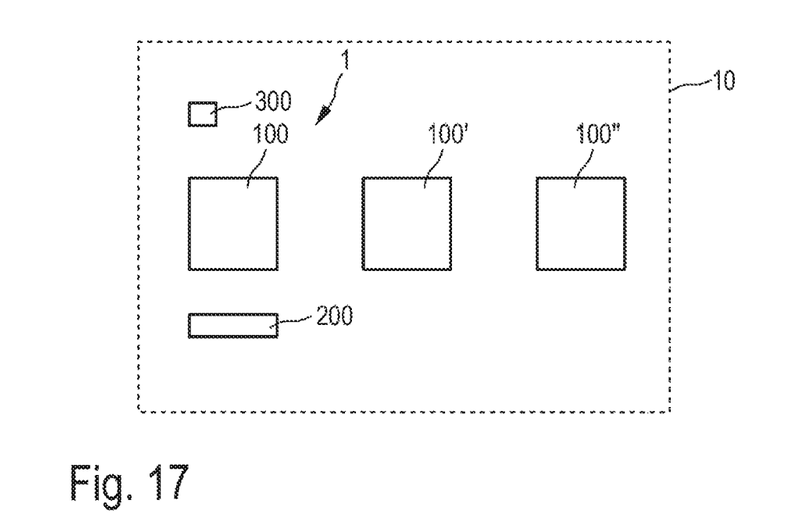
FIG. 17 shows a simplified schematic block diagram of an embodiment of a surgical instrument system according to the disclosure.

FIG. 17 shows an embodiment of a surgical instrument system 10 according to the present disclosure. The surgical instrument system 10 has the surgical instrument 1 according to FIGS. 1-6 and moreover comprises further cutting blocks 100', 100". The cutting blocks 100, 100', 100" are also designated below as first cutting block 100, second cutting block 100' and third cutting block 100". The cutting blocks 100, 100', 100" are different in terms of their dimensions and are provided for use on femoral bones of different sizes. Setting aside the different dimensions, the second cutting block 100' and the third cutting block 100" have a function and design identical to the first cutting block 100.

The reference foot 200 and the probe 300 are each able to be mounted on each of the cutting blocks 100, 100', 100". This by means of the above-described fastening recesses and fastening elements.

Figure 18:
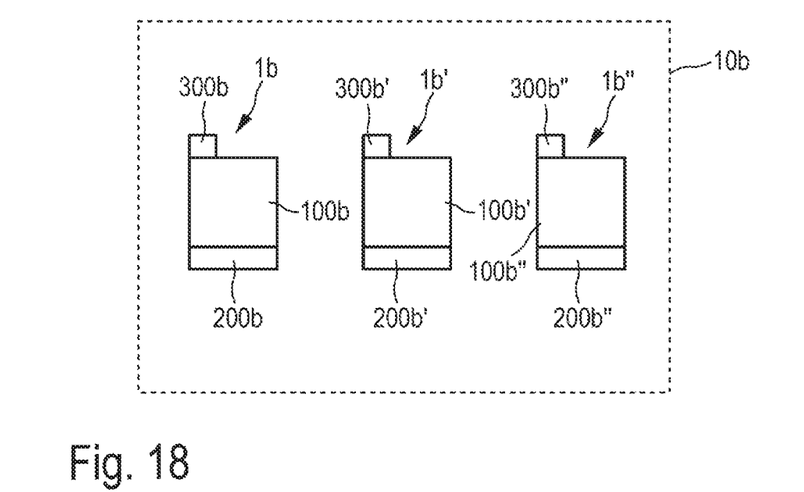
FIG. 18 shows, in a manner corresponding to FIG. 17, a further embodiment of a surgical instrument system according to the disclosure.

FIG. 18 shows a further embodiment of a surgical instrument system 10b according to the present disclosure. The surgical instrument system 10b has a surgical instrument 1b, which once again comprises a cutting block 100b, a reference foot 200b and a probe 300b. In terms of its function and design, the surgical instrument 1b is substantially identical to the surgical instrument 1 according to FIGS. 1-6. The first difference is the way in which the reference foot 200b and the probe 300b are fastened to the cutting block 100b. Instead of a releasable fastening, the reference foot 200b and the probe 300b in the surgical instrument 1b are each mounted permanently on the cutting block 100b. Permanently signifies that the reference foot 200b and the probe 300b are not each configured to be placed on and removed from the cutting block 100b. Instead, permanent joining connections (not shown or described in any detail) are present on the one hand between the reference foot 200b and the cutting block 100b and on the other hand between the probe 300b and the cutting block 100b.

The surgical instrument system 10b also has further surgical instruments 1b', 1b". The surgical instruments 1b, 1b', 1b" are designated below as first surgical instrument 1b, second surgical instrument 1b' and third surgical instrument 1b". The surgical instruments 1b, 1b', 1b" are different in terms of their dimensions and are provided for use on femoral bones of different sizes. Here, the surgical instruments 1b, 1b', 1b" differ at least in terms of a mediolateral dimension of the respective cutting block 100b, 100b', 100b". Moreover, the respective probe 300b, 300b', 300b" can have different dimensions, in particular along the proximodistal axis. The same may apply in the case of the respective reference foot 200b, 200b', 200b".

The invention claimed is:

1. A surgical instrument for use in a knee joint replacement operation, the surgical instrument comprising:
   a cutting block with a block rear face that is proximally oriented and configured to bear on a distal end face of a femur, the cutting block comprising at least one guide slot that extends from the block rear face to a block front face distally opposite the block rear face, the at least one guide slot being elongate in a mediolateral direction and configured to receive and guide a saw blade;
   a reference foot that is mountable or mounted on the cutting block at a block lower face of the cutting block, the reference foot having a foot upper face that is anteriorly oriented and protrudes proximally beyond the block rear face in a mounted state of the reference foot, the foot upper face being configured to bear on posterior condyles of the femur; and
   a probe that is mountable or mounted on the cutting block at a block upper face lying anteriorly opposite the block lower face, the probe comprising a probe tip which, in a mounted state of the probe, protrudes proximally beyond the block rear face and is configured to bear on an anterior face of the femur,
   the reference foot comprising a fastening element and at least one separating gap that extends in an anteroposterior direction and is substantially U-shaped in longitudinal extent so as to form a spring tongue portion that is elastically resiliently movable.

2. The surgical instrument according to claim 1, wherein the cutting block has a first fastening recess that is posteriorly arranged, wherein the fastening element is complementary to the first fastening recess, and wherein the first fastening recess and the fastening element are releasably connectable or connected to each other with form-fit and/or force-fit engagement.

3. The surgical instrument according to claim 2, wherein the first fastening recess is a receiving slot that extends from the block rear face to the block front face, the receiving slot being straight and elongate in the mediolateral direction, and wherein the fastening element is a plug element that is flat and plate-shaped, the plug element being configured to be plugged with form-fit and/or force-fit engagement into the receiving slot.

4. The surgical instrument according to claim 3, wherein the spring tongue portion, in the mounted state of the reference foot, is biased against an inner wall of the receiving slot.

5. The surgical instrument according to claim 3, wherein the receiving slot has two separate slot portions that are separated from each other in the mediolateral direction by a web, and the plug element has two plug portions that are separated from each other in the mediolateral direction by a gap.

6. The surgical instrument according to claim 3, wherein the receiving slot, in a non-mounted state of the reference foot, is configured to receive and guide the saw blade and forms a posterior guide slot of the cutting block.

7. The surgical instrument according to claim 2, wherein the reference foot forms an extension that is flat and plate-shaped, the extension being spaced apart from the fastening element and comprising an upper face that forms the foot upper face.

8. The surgical instrument according to claim 7, wherein the reference foot has a grip portion that is distally arranged, wherein the fastening element and/or the extension protrudes in a proximal direction from the grip portion, and wherein the grip portion has a first grip surface that is laterally oriented, a second grip surface that is medially oriented, and a stop surface that is proximally oriented.

9. The surgical instrument according to claim 1, wherein the cutting block has a second fastening recess that is anteriorly arranged, wherein the probe has a fastening element that is complementary to the second fastening recess, and wherein the second fastening recess and the fastening element of the probe are releasably connectable or connected to each other with form-fit and/or force-fit engagement.

10. The surgical instrument according to claim 9, wherein the second fastening recess is designed as a constituent part of a universal fastening system and is configured for connection to further instrument components.

11. The surgical instrument according to claim 9, wherein the second fastening recess has a latch recess that is sunk posteriorly into the block upper face, is elongate in the mediolateral direction and is open at a medial or lateral end, and wherein the fastening element of the probe has a latch portion that is complementary to and interacts with the latch recess to form a releasable snap-fit connection.

12. The surgical instrument according to claim 9, wherein the second fastening recess has a plug recess that extends mediolaterally into a block outer face of the cutting block, and wherein the fastening element of the probe has a plug portion that is complementary to and interacts with the plug recess to form a releasable plug connection.

13. The surgical instrument according to claim 1 further comprising a plurality of different compensation elements having different anteroposterior thicknesses, the different compensation elements each being mountable onto the foot upper face, the different compensation elements being configured to compensate for different degrees of wear of the posterior condyles.

14. The surgical instrument according to claim 1, wherein the reference foot and the probe are each mounted permanently on the cutting block.

15. A surgical instrument system comprising the surgical instrument according to claim 1,
wherein the surgical instrument system comprises a plurality of different cutting blocks that includes the cutting block,
wherein the plurality of different cutting blocks differ from one another in terms of at least one dimension, and
wherein the reference foot and the probe are each mountable on each of the plurality of different cutting blocks.

16. A surgical instrument system comprising a plurality of surgical instruments according to claim 1,
wherein, for each surgical instrument, the reference foot and the probe are mounted permanently on the cutting block, and
wherein the plurality of surgical instruments differ from one another in terms of at least one dimension of the cutting block.

\* \* \* \* \*